United States Patent [19]

De Feo et al.

[11] 4,335,246

[45] Jun. 15, 1982

[54] SUBSTITUTED ARYLAMINE INTERMEDIATES FOR DYES

[75] Inventors: Francesco De Feo, Milan; Giovanni Burei, Seregno; Roberto Cipolli, Novara, all of Italy

[73] Assignee: Aziende Colori Nazionali Affini ACNA S.p.A., Milan, Italy

[21] Appl. No.: 78,378

[22] Filed: Sep. 24, 1979

Related U.S. Application Data

[62] Division of Ser. No. 934,676, Aug. 18, 1978, abandoned.

[30] Foreign Application Priority Data

Aug. 23, 1977 [IT] Italy .............................. 26872 A/77

[51] Int. Cl.$^3$ ............... C07D 213/74; C07C 125/065; C07C 143/78
[52] U.S. Cl. .................................... 546/309; 560/13; 560/14; 560/28; 560/29; 560/31; 560/32; 560/164; 560/12; 560/45; 560/106; 560/193; 560/221; 560/227; 560/228; 560/252; 562/452; 260/465 D

[58] Field of Search ................. 546/309; 560/13, 14, 560/28, 29, 31, 32, 164

[56] References Cited

U.S. PATENT DOCUMENTS

| | | | |
|---|---|---|---|
| 2,693,407 | 11/1954 | Swezey | 560/228 |
| 3,076,838 | 2/1963 | La Combe et al. | 560/221 |
| 3,862,210 | 1/1975 | Murayama et al. | 560/32 |

OTHER PUBLICATIONS

Colour Index, vol. 3, 2nd Ed., (1956, Lowell Tech. Institute, Lowell, Mass.), pp. 3009, 3013, 3017–3018.
Moritz et al., Chem. Abst. 1974, vol. 80, 38368r.
Butler et al., JACS 1938, vol. 60, pp. 1582–1584.

*Primary Examiner*—Henry R. Jiles
*Assistant Examiner*—Natalia Harkaway
*Attorney, Agent, or Firm*—Morgan, Finnegan, Pine, Foley & Lee

[57] ABSTRACT

Substituted arylamine dye intermediates and their preparation are disclosed.

11 Claims, No Drawings

SUBSTITUTED ARYLAMINE INTERMEDIATES FOR DYES

CROSS-REFERENCE TO RELATED APPLICATION

This is a divisional of copending application Ser. No. 934,676, filed Aug. 18, 1978, now abandoned.

This invention relates to a new class of intermediates that are predominantly utilized in the preparation of dyes for textile materials.

In particular the present invention relates to the preparation of the new intermediates of general formula (I):

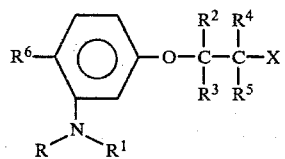

wherein

R and R', like or unlike each other, may be H; an alkyl $C_1-C_4$ optionally substituted by halogen, CN, $CONH_2$, COO alkyl $C_1-C_4$, aryloxy, alkyl $C_1-C_{12}$-aryloxy, alkoxy $C_1-C_4$ groups; an aralkyl;

$R^2$ is H; alkyl $C_1-C_{18}$; vinyl; halogen; aryl; aralkyl $C_{1-C4}$; mono- and tri-halogen methyl; hydroxymethyl; acyl ($C_1-C_4$) oxymethyl; dialkyl ($C_1-C_4$) amino methyl; alkoxy $C_1-C_4$ methyl;

$R^3$ is H; alkyl $C_1-C_2$; halogen alkyl $C_1-C_3$; trihalogen methyl; hydroxyl;

$R^4$ is H; alkyl $C_1-C_3$; halogen alkyl $C_1-C_3$; trihalogen methyl; carbalkoxy $C_1-C_4$; carboxyl;

$R^5$ is H; alkyl $C_1-C_2$; two out of $R^2$, $R^3$, $R^4$ and $R^5$ may form together a penta or hexa-atomic aliphatic cycle, the other two being H; $R^6$ is H; halogen; alkyl $C_1-C_4$; optionally substituted alcoxyl $C_{1-C4}$;

X is OCO alkyl $C_1-C_{18}$ optionally substituted by halogen, COOH, CN; OCO alkene $C_2-C_{18}$; OCO aryl, optionally substituted; OCOO alkyl $C_1-C_{18}$; optionally substituted OCOO aryl; OCOO aralkyl; OCOO cycloalkyl; optionally substituted $OSO_2$ aryl; $OSO_2$ alkyl $C_1-C_4$; OCOHN alkyl $C_1-C_4$; OCOHN halogenalkyl $C_1-C_4$; OCOHN aryl optionally substituted by one or more of the following groups: halogen, alkyl $C_1-C_4$, alkoxyl $C_1-C_4$, $SO_3H$, COOH, $SO_2NH_2$, $SO_2NH$ acyl; O alkyl $C_1-C_4$ optionally substituted by CN, $CONH_2$, CON (alkyl $C_1-C_4$)$_2$, COOH, COO alkyl $C_1-C_4$; $OCOHNO_2S$ alkyl $C_1-C_4$; $OCOHNO_2S$ aryl, optionally substituted;

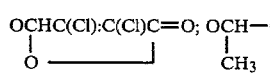

alkyl $C_1-C_{18}$; halogen; $N(R^7R^8)$; $N(NH_2)C-(NH_2)=NH$; $NHC(NH_2)=NH$;

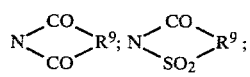

N(acyl)$_2$; OCONH-naphtyl optionally substituted by halogen; —OCOHN—$C_5H_4N$; —OCON($C_1-C_4$ alkyl)$_2$. $R^7$ and $R^8$, like or unlike each other, are alkyl $C_1-C_4$; together they may form a cycle either optionally substituted or containing other heteroatoms; $R^9$ may be alkylene optionally substituted by COOH, $SO_3H$, $SCH_2COOH$; or arylene optionally substituted by COOH, $SO_3H$, $SO_2NH_2$, $SO_2NH$ acyl.

OBJECTS OF THE INVENTION

An object of this invention is to provide novel dye intermediates with a high degree of purity in a simple and effective manner. Further objects of the invention will be apparent from the discussion which follows:

GENERAL DESCRIPTION OF THE INVENTION

The intermediate compounds of general formula (I) are synthetized according to known reactions by condensation or addition of the products of general formula (II):

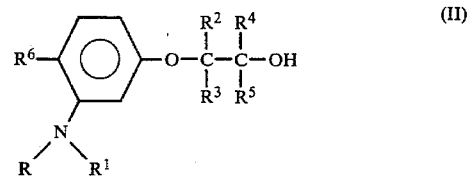

with known reagents having the following general formulae:

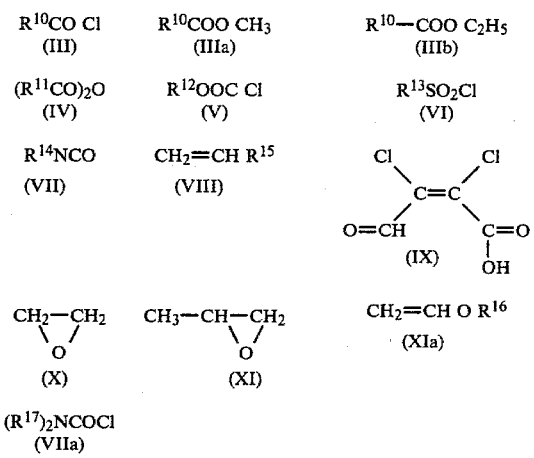

$(R^{17})_2NCOCl$
(VIIa)

wherein:
R, $R^1$, $R^2$, $R^3$, $R^4$, $R^5$, $R^6$, $R^7$, $R^8$ and $R^9$ have the meaning specified hereinbefore, and:

$R^{10}$ is alkyl $C_1-C_{18}$ optionally substituted by halogen or CN; alkene $C_2-C_{18}$; optionally substituted aryl;

$R^{11}$ is alkyl $C_1-C_{18}$; together they may be an aryl residue or a saturated or unsaturated aliphatic bridge;

$R^{12}$ is alkyl $C_1-C_{18}$; optionally substituted aryl, aralkyl, cycloalkyl;

$R^{13}$ is an optionally substituted aryl; alkyl $C_1-C_4$;

$R^{14}$ is alkyl $C_1-C_4$; halogen alkyl $C_1-C_4$; aryl, optionally substituted by one or more groups of halogen, alkyl $C_1-C_4$, alkoxyl $C_1-C_4$, $SO_3H$, COOH; $SO_2$ alkyl $C_1-C_4$; $SO_2$ aryl, optionally substituted; naphtyl optionally substituted by halogen;

$R^{15}$ is CN, $CONH_2$, CON(alkyl $C_1-C_4$)$_2$, COOH, COO alkyl $C_1-C_4$; $C_5H_4N$;

$R^{16}$ is alkyl $C_1-C_{18}$;

$R^{17}$ is alkyl $C_1$-$C_4$, or by condensation of the products having general formula (XII):

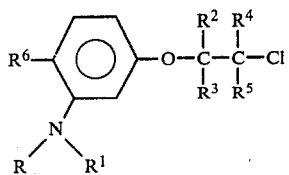

obtainable, for example, from the intermediates of general formula (II) by reaction with $POCl_3$, conforming to the process described in the examples, with derivatives having the following general formulae:

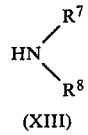 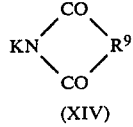 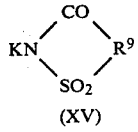

  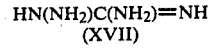

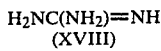

where:
R, $R^1$, $R^2$, $R^3$, $R^4$, $R^5$, $R^6$, $R^7$, $R^8$, and $R^9$ have the meaning defined hereinbefore.

The reactions of the compounds having general formulae (II) and (XII) with the reagents having structures comprised in formulae from (III) to (XIa) and from (XIII) to (XVIII) respectively, are usually conducted in the presence of aprotic solvents, such as benzene, toluene, xylene, chlorobenzene, orthodichlorobenzene, pyridine, dimethylformamide, dimethylacetamide, dimethylsulphoxide, hexamethylphosphoramide, at temperatures ranging from 0° and 140° C. in the presence or in the absence of hydrogen acceptors, such as triethylamine, or of basic catalysts, such as quaternary ammonium salts or pyridine, the separation of the product from the reaction mass being generally carried out in cold conditions by simple filtration.

The products so obtained usually have a high purity degree and are utilized as such in the successive synthesis step to dye.

These intermediates, in fact, are mainly employed to prepare disperse dyes of the styryl type or of the azo type. Furthermore it is possible to obtain acid azo dyes, direct dyes, solvent dyes and cationic dyes suited to dye acrylic fibres.

The intermediates of general formula (II) are known in part and can be synthetized by oxyethylation reaction of the phenols having general formula (XIX):

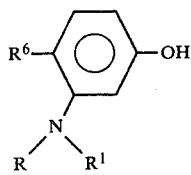

where R, $R^1$ and $R_6$ have the meaning specified hereinbefore, for example with ethylene oxide or ethylene chlorohydrin and derivatives thereof, according to the method illustrated by Butler and Renfrew, J. Am. Chem. Soc. 60 (1938) 1582-85.

SPECIFIC DESCRIPTION OF THE INVENTION

The following examples are given to illustrate the characteristics of the present invention, without being however a limitation thereof.

Unless otherwise specified, "parts" are to be intended as expressed in weight unit.

EXAMPLE 1

41.8 parts of intermediate (A):

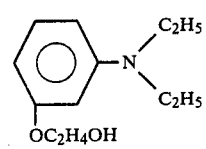

and 30 parts of acetic anhydride were kept at reflux for 2 hours, controlling the reaction trend by a thin-layer chromatographic analysis (carrier: silica gel; eluent: toluene 30,; ethyl acetate 10, pyridine 8, $NH_4OH$ 2 by volume) and then developing the chromatographic plate with a diazonium salt solution.

At the end, the solution was allowed to cool to room temperature, whereupon it was poured onto 300 parts of ice under intense stirring. The resulting precipitate was separated by filtration, it was washed with water to neutral pH and dried in air. There were recovered 42.3 parts of intermediate

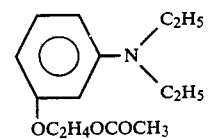

in the form of a grey-pink powder, having the following elemental analysis:

| calculated % | 66.906 | 8.422 | 5.573 |
| --- | --- | --- | --- |
| | C | H | N |
| found % | 66.4 | 8.35 | 5.49 |

EXAMPLE 2

20.9 parts of intermediate (A) of example 1 were reacted with 12.5 parts of phenyl isocyanate in the presence of 60 ml of ortho-dichlorobenzene at a temperature of 80° C. The reaction was controlled by a thin-layer chromatographic analysis conducted according to example 1; at the conclusion of the addition, that lasted about 2 hours, the solution was allowed to cool under stirring and the resulting precipitate was separated by filtration and washed with a little amount of petroleum ether. 28.2 parts of the product:

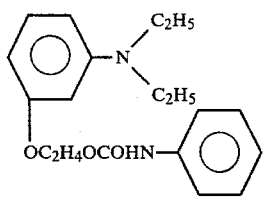

were recovered as a white powder, having a melting point=114°–116° C. and the following elemental analysis:

| calculated % | 69.488 | 7.366 | 8.531 |
|---|---|---|---|
|  | C | H | N |
| found % | 69.6 | 7.3 | 8.5 |

23.6 parts of such intermediate were added in small portions—so as to keep the temperature below 40° to 87 parts of sulphuric chlorohydrin. The mass was then heated 2 hours to 40° C., cooled down to 0° C. and finally poured onto 200 parts of ice. The resulting sulphochloride was separated by filtration and reacted with 150 ml of $NH_4OH$, under intense stirring, at 20° C. for 8 hours. A complete solution was first obtained, whereupon a precipitate formed, that was filtered and washed with water. The resulting cake was dried, thus recovering 14.3 parts of intermediate:

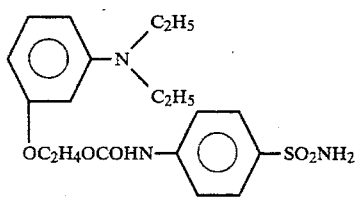

as a white powder having a melting point=193°–194° C., and the following elemental analysis:

| calculated % | 56.002 | 6.184 | 10.313 |
|---|---|---|---|
|  | C | H | N |
| found % | 55.6 | 6.08 | 10.2 |

EXAMPLE 3

Following exactly the method described in example 2, 20.9 parts of intermediate (A) of example 1 were reacted with 19.5 parts of 3,4-dichlorophenyl isocyanate in 60 ml of ortho-dichlorobenzene. There were recovered 37.2 parts of the intermediate:

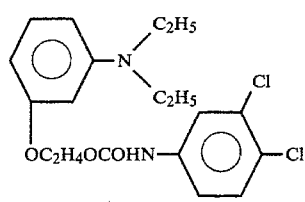

in the form of a white crystalline powder having a melting point=123.5°–125° C. and the following elemental analysis:

| calculated % | 57.438 | 5.581 | 7.052 | 17.848 |
|---|---|---|---|---|
|  | C | H | N | Cl |
| found % | 57.4 | 5.6 | 7.0 | 18.3 |

EXAMPLE 4

Following the method described in example 2, 22.3 parts of intermediate (B):

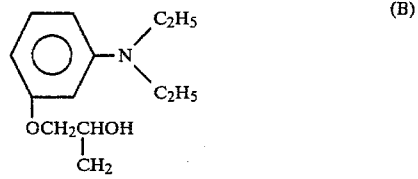

(B)

were reacted with 12.5 parts of phenyl isocyanate in the absence of solvent. 31.3 parts of intermediate:

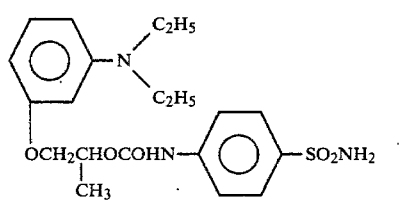

were recovered in the form of a white crystalline powder having a melting point=87°–89° C. and the following elemental analysis:

| calculated % | 70.149 | 7.653 | 8.181 |
|---|---|---|---|
|  | C | H | N |
| found % | 70.1 | 7.8 | 8.2 |

25.7 parts of such intermediate were added in small portions, in order to maintain a temperature lower than 40° C., to 87 parts of sulphuric chlorohydrin. The mass was then heated to 40° C. for 2 hours, cooled down to 0° C. and lastly poured onto 200 parts of ice. The resulting sulphochloride was separated by filtration and reacted with 150 parts of $NH_4OH$ under intense stirring for about 8 hours at 20° C. A solution was first obtained, whereupon a precipitate formed, that was separated by filtration and washed with water. By drying the cake 18.7 parts of intermediate:

were recovered in the form of a white powder having a melting point=97°–100° C. and the following elemental analysis:

| calculated % | 56.988 | 6.457 | 9.969 |
|---|---|---|---|
|  | C | H | N |

| -continued | | | |
|---|---|---|---|
| found % | 56.2 | 6.2 | 9.82 |

EXAMPLE 5

22.3 parts of intermediate (B) of example 4 were reacted with 19.5 parts of 3,4-dichloro-phenyl-isocyanate in the presence of 50 ml of ortho-dichlorobenzene according to the modalities described in example 1. 38.2 parts of the intermediate:

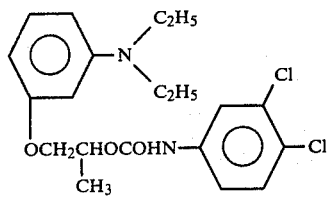

were recovered as a white crystalline powder having the following elemental composition:

| calculated % | 58.399 | 5.881 | 6.811 | 17.240 |
|---|---|---|---|---|
| | C | H | N | Cl |
| found % | 58.1 | 5.82 | 6.47 | 17.9 |

EXAMPLE 6

20.9 parts of intermediate (A) of example 1 and 11.0 parts of butyl isocyanate were reacted according to the modalities described in example 2 in the absence of solvent. 26.4 parts of the intermediate

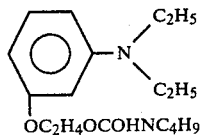

were recovered in the form of a white crystalline powder, having a melting point = 64°–65° C. and the following elemental analysis:

| calculated % | 66.203 | 9.151 | 9.083 |
|---|---|---|---|
| | C | H | N |
| found % | 66.3 | 9.7 | 9.2 |

EXAMPLE 7

20.9 parts of intermediate (A) of example 1 were reacted in 60 ml of xylene with 12 parts of succinic anhydride and 2.0 parts of pyridine at 90° C. for about 4 hours, checking the reaction trend by a thin-layer chromatographic analysis (carrier: silica gel; elents: butyl alcohol 20, isopropyl alcohol 20, acetic acid 10, water 10 parts by volume) and developing then the chromatographic plate with a solution of a diazonium salt. After distillation of the solvent, 28.2 parts of the intermediate:

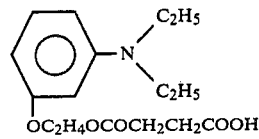

were recovered in the form of a purple thick liquid having the following elemental analysis:

| calculated % | 62.119 | 7.494 | 4.528 |
|---|---|---|---|
| | C | H | N |
| found % | 61.7 | 7.31 | 4.12 |

EXAMPLE 8

20.9 parts of intermediate (A) of example 1 were dissolved with 50 ml of pyridine; the solution was cooled to 0°–10° C., whereupon 20 ml of methyl chloroform-ate were gradually added thereto. The reaction was controlled by a thin-layer chromatographic analysis (under the conditions specified in example 1), keeping the whole at 0°–10° C. for about 3 hours, whereupon the solution was poured onto 400 parts of water, transferred into a separatory funnel and extracted with ethyl ether. After distillation of the solvent 25.4 parts of the intermediate:

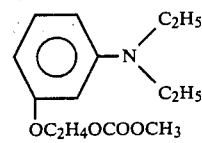

were recovered in the form of an orange-brown liquid having the following elemental analysis:

| calculated % | 62.901 | 7.918 | 5.240 |
|---|---|---|---|
| | C | H | N |
| found % | 62.3 | 7.58 | 5.28 |

EXAMPLE 9

209 parts of intermediate (A) of example 1 were additioned, at 35° C., with 153 parts of $POCl_3$, whereupon the mixture was heated to 80° C. for 1 hour. After cooling to room temperature, the mass was poured onto 500 parts of ice and 100 parts of water, and alkalized with 20% sodium hydrate. It was stirred for about 30 minutes, then the mass was transferred into a separatory funnel and treated with 50 parts of NaCl to enhance the separation of the two layers. The organic upper layer was recovered and subjected to a rectification process for recovering 180 parts of the intermediate:

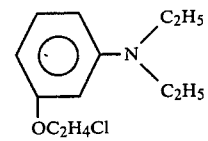

that was collected, as a thick brownish-red thick oil, at 128°–131° C. under a vacuum of 3.5 mm Hg. The product exhibited the following elemental analysis:

| | C | H | N | Cl |
|---|---|---|---|---|
| calculated % | 63.288 | 7.967 | 6.151 | 15.569 |
| found % | 62.4 | 7.9 | 6.5 | 15.7 |

EXAMPLE 10

68.3 parts of the intermediate of example 9, 82.1 parts of 2-methyl-imidazole and 38.3 parts of triethylamine were reacted at 115° C. in 300 ml of monochlorobenzene for 4–5 hours. At the conclusion of the reaction, the mass was allowed to cool to room temperature, whereupon the triethylamine chlorhydrate crystals were filtered by washing the cake with 50 ml of monochlorobenzene. The solution, having a brown colour, was subjected to distillation. There were recovered 72 parts of the product:

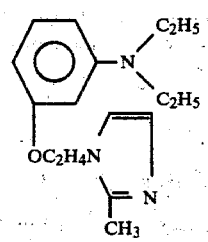

that precipitated, due to cooling, in the form of a brown powder having a melting point at 42°–46° C. and the following elemental analysis:

| | C | H | N |
|---|---|---|---|
| calculated = | 70.295 | 8.480 | 15.372 |
| found % | 69.6 | 8.2 | 15.7 |

EXAMPLE 11

68.3 parts of the intermediate of example 9, 45.1 parts of dimethylamine and 38.3 parts of triethylamine were reacted at 115° C. in 300 ml of monochlorobenzene for 4–5 hours in an autoclave, at a maximum pressure of 2.5 atm. The mass was then allowed to cool to room temperature and the dark liquid collected was put into a separatory funnel. The lower layer was repeatedly extracted with dilute HCl; the acid aqueous solution was then treated with 30% NaOH and brought to a pH = 10; finally the aqueous phase was removed by a separatory funnel. By distillation of the organic layer there were recovered 56.4 parts of the intermediate:

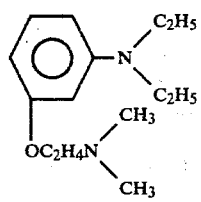

as a dark brown liquid that exhibited the following elemental analysis:

| | C | H | N |
|---|---|---|---|
| calculated % | 71.143 | 10.235 | 11.853 |
| found % | 70.9 | 10.4 | 12.02 |

EXAMPLE 12

36 parts of potassium phthalimide were added to 120 ml of dimethylsulphoxide; the mixture was heated to 95° C. and at such temperature a solution consisting of 33.0 parts of the intermediate of example 9 and of 30 ml of dimethylsulphoxide was additioned in 1 hour. The temperature was brought to 100° C. and the mass was stirred at such temperature for 6 hours, controlling the reaction trend by thin-layer chromatographic analysis (according to the conditions specified in example 1). It was cooled to room temperature and the mass was poured onto 400 parts of ice: the resulting precipitate was separated by filtration and washed with water. By drying the cake 43.6 parts of the intermediate:

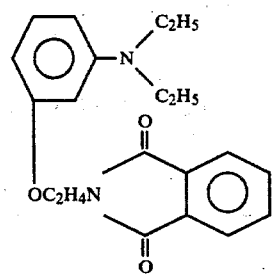

were obtained in the form of a yellow crystalline powder, having a melting point = 124°–125° C. and the following elemental analysis:

| | C | H | N |
|---|---|---|---|
| calculated % | 70.984 | 6.553 | 8.279 |
| found % | 70.6 | 6.5 | 8.1 |

EXAMPLE 13

Following exactly the procedure described in example 2, 20.9 parts of intermediate (A) of example 1 were reacted with 16.9 parts of naphthyl isocyanate in 30 ml of orthodichlorobenzene.

33.9 parts of the intermediate:

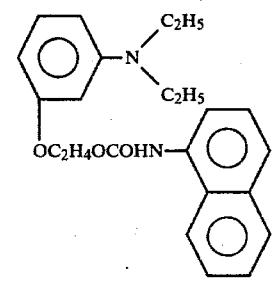

were recovered as a white crystalline powder having a melting point = 103°–106° C. and the following elemental analysis:

| | C | H | N |
|---|---|---|---|
| calculated % | 73.01 | 6.88 | 7.4 |

| | | | |
|---|---|---|---|
| | -continued | | |
| found % | 73.05 | 6.85 | 7.38 |

EXAMPLE 14

20.9 parts of intermediate (A) of example 1, 22 parts of dimethyl carbamoyl chloride and 11 parts of triethylamine were reacted at 100° C. in 40 ml of orthodichlorobenzene for 6–7 hours. At the conclusion of the reaction the mass was allowed to cool to room temperature, whereupon it was filtered whilst simulteneous removal of the solvent. The cake was dissolved again with water, the dispersion was stirred for 1 hour, then it was filtered and washed with water. By drying the cake, 42 parts of the intermediate:

[structure: phenyl with N(C$_2$H$_5$)$_2$ and OC$_2$H$_4$OCON(CH$_3$)$_2$]

were recovered as a greyish white powder having a melting point=56°–58° C. and the following elemental analysis:

| | C | H | N |
|---|---|---|---|
| calculated % | 64.28 | 8.57 | 10.0 |
| found % | 64.2 | 8.49 | 9.88 |

EXAMPLE 15

14.8 parts of isonicotinylazide were treated with boiling toluene until full removal of nitrogen. At the conclusion of nitrogen evolvement (about 20 minutes), 20.9 parts of intermediate (A) of example 1 were added to the toluene solution of the pyridine isocyanate that had formed, whereupon the mass was stirred for about 4 hours, always at the boiling temperature. The whole was then allowed to cool down to room temperature and the resulting precipitate was separated by filtration and washed with a few petroleum ether. After drying 29.6 parts of the intermediate:

[structure: phenyl with N(C$_2$H$_5$)$_2$ and OC$_2$H$_4$OCOHN-pyridyl]

were recovered as a white crystalline solid, having a melting point=167.5°–168.5° C. and the following elemental analysis:

| | C | H | N |
|---|---|---|---|
| calculated % | 65.65 | 6.99 | 14.59 |
| found % | 66.1 | 7.05 | 14.6 |

We claim:
1. A compound having the formula

[structure showing:

$$R^6\text{-phenyl}(NRR^1)\text{-O-}\underset{R^3}{\underset{|}{\overset{R^2}{\overset{|}{C}}}}\text{-}\underset{R^5}{\underset{|}{\overset{R^4}{\overset{|}{C}}}}\text{-X}$$]

wherein:
R and $R^1$, either like or unlike each other, may be H; or alkyl $C_1$–$C_4$;
$R^2$ is H; or alkyl $C_1$–$C_{18}$;
$R_3$, $R_4$ and $R_5$ are H;
$R^6$ is H; halogen; alkyl $C_1$–$C_4$; or alkoxy $C_1$–$C_4$; and
X is OCOHN alkyl $C_1$–$C_4$; OCOHN halogen alkyl $C_1$–$C_4$; OCOHN phenyl optionally substituted by one or more of the following groups: halogen, alkyl $C_1$–$C_4$, alkoxyl $C_1$–$C_4$, SO$_3$H, COOH, SO$_2$NH$_2$, and SO$_2$NH acyl; or —OCON(C$_1$–C$_4$ alkyl)$_2$.

2. The product:

[structure: phenyl-N(C$_2$H$_5$)$_2$ with OC$_2$H$_4$OCOHN-phenyl]

3. The product:

[structure: phenyl-N(C$_2$H$_5$)$_2$ with OC$_2$H$_4$OCOHN-phenyl-SO$_2$NH$_2$]

4. The product:

[structure: phenyl-N(C$_2$H$_5$)$_2$ with OC$_2$H$_4$OCOHN-phenyl(Cl)(Cl)]

5. The product:

[structure: phenyl-N(C$_2$H$_5$)$_2$ with OCH$_2$CH(CH$_3$)OCOHN-phenyl]

6. The product:

7. The product:
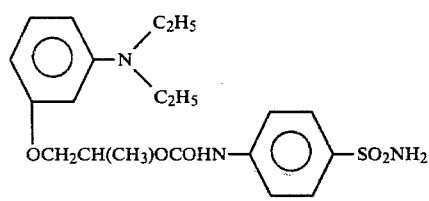
8. The product:
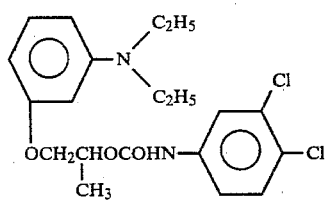
9. The product:
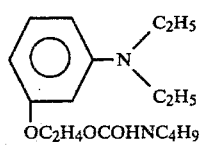
10. The product:
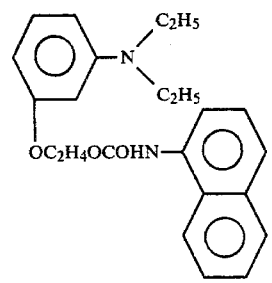
11. The product:
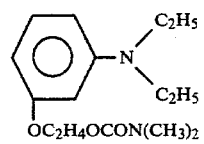
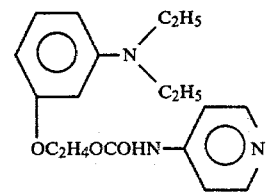
* * * * *